United States Patent
Layus et al.

(10) Patent No.: US 11,052,121 B2
(45) Date of Patent: Jul. 6, 2021

(54) USE OF A BACTERIAL COMPOSITION FOR TREATING FOOT INFECTIONS OF UNGULATES

(71) Applicant: Nolivade, Change (FR)

(72) Inventors: Michel Layus, Pleumeur Bodou (FR); Alexandre Brame, Rennes (FR)

(73) Assignee: Nolivade, Change (FR)

( * ) Notice: Subject to any disclaimer, the term of this patent is extended or adjusted under 35 U.S.C. 154(b) by 133 days.

(21) Appl. No.: 16/465,468

(22) PCT Filed: Nov. 30, 2017

(86) PCT No.: PCT/FR2017/053290
§ 371 (c)(1),
(2) Date: Dec. 31, 2019

(87) PCT Pub. No.: WO2018/100292
PCT Pub. Date: Jun. 7, 2018

(65) Prior Publication Data
US 2020/0179465 A1    Jun. 11, 2020

(30) Foreign Application Priority Data

Nov. 30, 2016 (FR) ..................................... 1661749

(51) Int. Cl.
*A61K 35/744* (2015.01)
*A61P 31/04* (2006.01)

(52) U.S. Cl.
CPC ............ *A61K 35/744* (2013.01); *A61P 31/04* (2018.01)

(58) Field of Classification Search
None
See application file for complete search history.

(56) References Cited

U.S. PATENT DOCUMENTS

2015/0250832 A1* 9/2015 De Brueker ............... A23L 2/38
424/93.3

FOREIGN PATENT DOCUMENTS

| FR | 3026643 A1 | 4/2016 | |
|---|---|---|---|
| WO | 98/47374 A1 | 10/1998 | |
| WO | 2013/178947 A1 | 12/2013 | |
| WO | 2014/151837 A1 | 9/2014 | |
| WO | WO-2017074485 A1 * | 5/2017 | ............... A61P 1/04 |

OTHER PUBLICATIONS

Bermudez-Brito et al. Ann Nutr Metab 2012; 61:160-174.*

* cited by examiner

*Primary Examiner* — Oluwatosin A Ogunbiyi
(74) *Attorney, Agent, or Firm* — Dinsmore & Shohl LLP

(57) ABSTRACT

The invention relates to the use of a bacterial mixture for the prevention and improvement of the state of ungulates suffering from pathologies involving a parasitic or bacterial infection of the foot, said composition comprising: at least one strain of bacteria of the genus *Bacillus*, and at least one lactic acid bacterium.

7 Claims, 5 Drawing Sheets

USE OF A BACTERIAL COMPOSITION FOR TREATING FOOT INFECTIONS OF UNGULATES

The invention relates to the use of a composition for treating animal diseases.

In modern bovine, caprine, and ovine farming, lameness is common and makes up a third of all visits by a veterinary practitioner. Podal disorders, whether or not they are the cause of lameness, are increasingly frequent in the context of current intensive farming. They have various etiologies, and the location thereof on the musculoskeletal system is variable. The dirty and abrasive environment around the feet is a factor that is often said to promote the occurrence of diseases that result in the animal becoming lame. Indeed, damp, dirty ground and abrasive concrete promote and maintain skin inflammation that underlies the observed lameness and the high level of recurrence of these disorders.

The combination of these stressors that contribute to causing pain and lameness in animals is called "abiotic stress". This abiotic stress causes abrasion to the interdigital spaces or to the digits themselves, which results in inflammatory reactions promoting the ingress of bacteria or other parasites, causing pododermatitis and lameness. It weakens the cutaneous barrier in particular and produces favorable conditions for podal ailments to become established and persist.

There are both antibiotics, such as oxytetracycline, as well as disinfectants for application in a foot bath on the market, but the frequency and duration of administration are not standardized. No indication is given of the necessity of using said antibiotics and disinfectants depending on the number of detected cases, and these foot baths are not always entirely practical to put in place. Some of these treatment products are reputed to be effective (formol, copper sulfate), but they risk being prohibited for use in the near future since they are a toxic risk to humans or the environment. In addition, the use of antibiotics is also subject to criticism and is restricted due to the risk of developing resistance.

This represents a limitation to the means available for controlling this disease, as the measures that have been implemented are inadequate for limiting the spread of diseases that result in animals becoming lame.

In addition, there is a need to provide effective treatments for treating animals and protecting their health, while respecting the environment.

Several approaches have been used to attempt to reduce lameness in ungulates. For example, the French application FR3026643A1 describes the use of aromatic plant extracts in combination with minerals for treating Mortellaro disease in cattle. The animals are treated by ingesting a dietary supplement containing said extracts, which causes their immune defenses to be stimulated. Another example is the international application WO1998047374, which describes the use of probiotics for preventing bacterial, fungal, or viral infections, the probiotics being *Bacillus* strains selected from: *Bacillus coagulans, Bacillus subtilis, Bacillus laterosporus* and *Bacillus laevolacticus*. These probiotics are used to treat dermatitis and contact dermatitis. The probiotics in question are applied directly to the skin or the mucosa to be treated. However, the efficacy thereof has not been formally demonstrated.

In addition, these methods do not seem to be the most effective and do not present a more general solution to the problem of lameness in ungulates.

In addition, the invention aims to overcome these drawbacks.

One of the objects of the invention is to propose a means for improving the quality of life of animals suffering from lameness.

Another object of the invention is to provide a composition having these properties.

The invention relates to a composition comprising a bacterial mixture for use in the prevention and improvement of the condition of ungulates suffering from diseases involving a bacterial or parasitic podal infection, said composition comprising:

at least one bacterial strain of the genus *Bacillus*, in particular at least one *Bacillus subtilis*, and at least one lactic bacterial strain, in particular at least one *Lactococcus lactis* and/or at least one *Pediococcus pentosaceus*.

The invention is based on the surprising finding by the inventors that the combination of bacteria of the genus *Bacillus* and lactic bacteria significantly improves the condition of ungulates suffering from lameness caused by a parasitic or bacterial podal infection.

In the invention, "diseases involving a parasitic or bacterial podal infection" means a disease of which the symptoms are linked to a bacterium, but also to a virus or a parasite (such as a mite or arthropod).

In the invention, as in zootechnics, "foot" means the end portion of the four limbs. Each foot comprises two functional digits; the external or lateral digit III and the internal or medial digit IV as well as two non-functional ancillary digits are located on the palmar surface of the foot, opposite the second phalanx. They are called dewclaws and are the vestiges of the digits II internally and the digits V externally. Here, the differential diagnosis of podal bovine diseases only takes into consideration the anatomical structures between the mandacarpophalangeal joint and the end of the front and rear limbs. This may also be referred to as the digital region.

In the invention, "ungulates" means animals having one or more hooves at the end of their limbs. The hoof is therefore a highly developed corneous formation that surrounds the digit(s) contacting the ground when walking. The ungulates covered by the present invention are in particular domestic ungulates, especially farmed ungulates, such as those in porcine, bovine, caprine, and ovine farming. The preferred ungulates are pigs, cows and calves, goats and sheep, and, to a lesser extent, horses.

The bacteria of the genus *Bacillus* used in the invention are gram-positive bacteria from the Bacillaceae family, the Bacillales order, the Bacillis class, and the Firmicutes phylum.

The lactic bacteria of the invention are gram-positive bacteria.

The inventors have demonstrated that the use of a combination of at least one *Bacillus* with at least one lactic bacterium had the effect of improving the quality of life of ungulates suffering from lameness due to a podal infection.

Advantageously, the invention relates to a composition for use as defined above, in which the bacterial composition contains:

at least one of the four following *Bacillus subtilis* strains: NOL01, NOL02, NOL03 and NOL04, said strains being deposited at the CNCM under the numbers CNCM I-4606, CNCM I-5043, CNCM I-4607 and CNCM I-4608, respectively, and at least one lactic bacteria selected from the following lactic bacteria: *Lactococcus lactis* spp *lactis* 1 strain NOL11 and *Pediococcus pentosaceus* 2 strain NOL12, said strains being deposited at the CNCM under the numbers CNCM I-4609 and CNCM I-4610, respectively.

The different strains of the invention, referenced by their deposit number, have all been deposited at the National Collection of Cultures of Microorganisms (CNCM), at the Institut Pasteur, in Paris (25,28 rue du Docteur Roux 75724 Paris CEDEX 15) in accordance with the Budapest Treaty.

The strain NOL01 was deposited under the number CNCM I-4606 on 14 Mar. 2012,

The strain NOL02 was deposited under the number CNCM I-5043, on 21 Jan. 2016,

The strain NOL03 was deposited under the number CNCM I-4607 on 14 Mar. 2012,

The strain NOL04 was deposited under the number CNCM I-4608 on 14 Mar. 2012,

The strain NOL11 was deposited under the number CNCM I-4609 on 14 Mar. 2012, and The strain NOL12 was deposited under the number CNCM I-4610 on 14 Mar. 2012.

The invention relates to the use of at least one strain selected from the strains NOL01, NOL02, NOL03 and NOL04, and at least one strain selected from the strains NOL11 and NOL12. In addition, the invention covers the 45 following combinations:

NOL01 and NOL11,
NOL01 and NOL 12,
NOL01, NOL11 and NOL 12,
NOL02 and NOL11,
NOL02 and NOL 12,
NOL02, NOL11 and NOL 12,
NOL03 and NOL11,
NOL03 and NOL 12,
NOL03, NOL11 and NOL 12,
NOL04 and NOL11,
NOL04 and NOL 12,
NOL04, NOL11 and NOL 12,
NOL01, NOL02 and NOL11,
NOL01, NOL02 and NOL12,
NOL01, NOL02, NOL11 and NOL12,
NOL01, NOL03 and NOL11,
NOL01, NOL03 and NOL12,
NOL01, NOL03, NOL11 and NOL12,
NOL01, NOL04 and NOL11,
NOL01, NOL04 and NOL12,
NOL01, NOL04, NOL11 and NOL12,
NOL02, NOL03 and NOL11,
NOL02, NOL03 and NOL12,
NOL02, NOL03, NOL11 and NOL12,
NOL02, NOL04 and NOL11,
NOL02, NOL04 and NOL12,
NOL02, NOL04, NOL11 and NOL12,
NOL03, NOL04 and NOL11,
NOL03, NOL04 and NOL12,
NOL03, NOL04, NOL11 and NOL12,
NOL01, NOL02, NOL03 and NOL11,
NOL01, NOL02, NOL03 and NOL12
NOL01, NOL02, NOL03, NOL11 and NOL12.
NOL01, NOL02, NOL04 and NOL11,
NOL01, NOL02, NOL04 and NOL12,
NOL01, NOL02, NOL04, NOL11 and NOL12,
NOL01, NOL03, NOL04 and NOL11,
NOL01, NOL03, NOL04 and NOL12,
NOL01, NOL03, NOL04, NOL11 and NOL12,
NOL02, NOL03, NOL04 and NOL11,
NOL02, NOL03, NOL04 and NOL12,
NOL02, NOL03, NOL04, NOL11 and NOL12,
NOL01, NOL02, NOL03, NOL04 and NOL11,
NOL01, NOL02, NOL03, NOL04 and NOL12, and
NOL01, NOL02, NOL03, NOL04, NOL11 and NOL12.

Advantageously, the invention relates to a composition for use as defined above, said composition containing from $10^5$ to $10^{11}$ bacterial *Bacillus* colonies and from $10^5$ to $10^{11}$ lactic-bacteria bacterial colonies, the bacterial colonies being by ml or g of composition.

In the invention, from $10^5$ to $10^{11}$ bacterial colonies means: approximately $10^5$, approximately $5.10^5$, approximately $10^6$, approximately $5.10^6$, approximately $10^7$, approximately $5.10^7$, approximately $10^8$, approximately $5.10^8$, approximately $10^9$, approximately $5.10^9$, approximately $10^{10}$, approximately $5.10^{10}$ or approximately $10^{11}$ bacterial colonies per ml of bacterial culture.

A person skilled in the art readily knows how to ascertain this number of bacteria, in particular either by manual counting (using a Malassez slide) or by using an automatic cell counter, or by dilution and then seeding on agar plates and counting the colonies.

More advantageously, the invention relates to a composition for use as defined above, wherein at least one *Bacillus* strain is in sporulated form and/or in vegetative form.

In particular, it is especially advantageous for the bacteria of the genus *Bacillus*, and in particular the strains NOL01, NOL02, NOL03 and NOL04 as defined above, to be in sporulated form and for the lactic bacteria strains to be in vegetative form.

Yet more advantageously, the invention relates to a composition for the above-mentioned use, in which said diseases involving a parasitic or bacterial infection in the feet of ungulates are selected from Mortellaro disease, interdigital dermatitis, or tyloma, paronychia or laminitis, or foot rot, bulb erosion, toe necrosis and pododermatitis.

Mortellaro disease, or digital dermatitis, was described for the first time in 1974 in Milan by Cheli and Mortellaro. It was evidenced in France in the 1980s. This disease appears to be increasingly frequent in French farming and poses a number of questions relating to the management thereof in the long term. It is considered to be the third most frequent podal infection after heel erosion (interdigital dermatitis) and sole hemorrhage (corns), Mortellaro disease is caused by *Treponema* and potentially by *Fusobacterium necrophorum*. Once introduced to a farm, it is very rarely eradicated and reoccurs in successive outbreaks. Digital dermatitis is a contagious ailment characterized by a circumscribed superficial inflammation of the skin of the coronet, which leads to lameness. It affects cattle in particular. Mortellaro disease is recognizable by a swollen foot and interdigital necrosis.

Interdigital dermatitis (called 'Le Fourchet' in French) is a bacterial infection. It is caused by a bacterium (*Dicheiobacter nodosus* and *Fusobacterium necrophorum*) which particularly likes warm, moist environments. Le Fourchet, or interdigital dermatitis, starts with a moist, malodorous inflammation of the interdigital skin and extends to the heel horn, where it affects the corneous sheath. The horn produced is of low quality and fissures arise in the heel bulb. These fissures cause irritation to the pododerm, which reacts by producing more horn, From this stage onwards, the situation only gets worse.

Tyloma, or interdigital hyperplasia, is a proliferative inflammatory reaction of the skin between the claws, but it is common to have Mortellaro lesions above. The pathology therefore results from infections caused by *Treponema* and *Fusobacterium necrophorum*.

Paronychia or interdigital phlegmon are acute soft-tissue inflammations characterized by a swollen, red hoof. These diseases are caused by bacteria, in particular *Arcanobacterium pyogenes* and *Fusobacterium necrophorum*.

Laminitis, or diffuse aseptic pododermatitis, is a lesion on the sole which gives a yellow/red color and may even go blue, and may develop into an ulcer.

Foot rot is a bacterial disease transmitted by pastures, bedding, or pathways contaminated by infected animals. This disease is characterized in the first instance by redness in the interdigital space, and then the animals become lame and have oozing lesions with an unpleasant odor. The horn then starts to rot, some parts of the claw necrotize and become detached from the animal's foot.

Bulb erosion is defined as the irregular loss of the horn of the bulb in the region of the heel, often in the form of deep oblique grooves. This bacterial infection causes rot in the heels. Toe necrosis is a lesion on the distal end of the feet of cattle, which causes lameness that is occasionally severe.

Pododermatitis is a bacterial infection of the skin that is generally situated around the claws or hooves of the feet. The following diseases have been identified in ungulates: aseptic pododermatitis (Pododermatitis aseptica acuta, Pododermatitis aseptica chronica), purulent pododermatitis (Pododermatitis purulenta), canker or chronic verrucous pododermatitis (Pododermatitis chronica verrucose), certain forms of gangrene (Pododermatitis gangraenosa), necrotizing pododermatitis (Pododermatitis necrotica), infectious pododermatitis (Pododermatitis infectiosa) and chronic hyperplastic pododermatitis (Pododermatitis chronica hyperplastica).

The above-mentioned composition may therefore be used as described above to improve the quality of life of animals suffering from lameness caused by the above-mentioned diseases. Indeed, the bacterial mixture of the invention has a limiting effect on the progression of the bacteria that cause said diseases.

The bacterial mixture also has a preventative effect, by limiting the proliferation of pathogenic bacteria, and therefore prevents the lameness resulting therefrom.

Advantageously, the invention relates to a composition for use as defined above, said composition being in a liquid form that is intended to be sprayed or used in a basin, The composition according to the invention is in particular provided in the form of powder but may also be provided in the form of liquid in order to be applied more easily to the feet of the ungulates. This application in liquid form may be carried out by being sprayed or nebulized directly onto already infected feet, or merely onto healthy feet for the purpose of prophylaxis. It is also possible to provide compositions in the form of liquids that are placed into foot baths through which the animals walk, which brings the composition of the invention into contact with the feet of the ungulates.

More advantageously, the invention also relates to a composition for the above-mentioned use, where said composition is diluted in at least one 1 liter of liquid but at most 5 liters of liquid for 50 to 60 animals.

In the context of the invention, it is advantageous for the above-mentioned bacterial composition to be diluted in a liquid volume of from 1 to 5 liters to treat 50 to 60 animals by spraying.

In the invention, "at least one 1 liter of liquid but at most 5 liters of liquid" specifies that the composition may be diluted in 1 l, 1.5 l, 2 l, 2.5 l, 3 l, 3.5 l, 4 l, 4.5 l, or 5 l, when there are 50 to 60 animals to be treated (or 100 to 120 rear feet, which are the feet that are affected most).

Volumes of approximately 1 l are particularly advantageous for an application that is in particular carried out by spraying onto the feet. The largest volumes, and in particular 5 l, are the most appropriate for foot baths. However, the largest volumes may be used for spraying or nebulizing.

For 100 animals, it is also possible to double the above-mentioned volumes in a proportional manner, and a person skilled in the art will know how to make the appropriate conversions.

The composition according to the invention, when it is diluted as mentioned above, is in particular in a liquid that is either water, saline water (0.9 wt. % salt saline solution based on the total volume), or any other liquid that is physiologically acceptable for cutaneous application or application to the horn of the hooves of the animals.

The liquid used may also contain physiologically acceptable additives, and in particular thiosulfate when the liquid is water. The thiosulfate in fact neutralizes the chlorine contained in the running water supplied by various water companies. The liquid may also contain salts and/or dyes. It is important that the additives do not have an influence on the vitality of the bacteria contained in the composition of the invention.

Advantageously, the invention relates to a composition for the above-mentioned use, where said composition is applied to the feet of the ungulates from once every 3 days to once every 15 days.

The appropriate treatment dosage for preventing lameness in the animals or for improving their quality of life is one use once every 3 days to once every two weeks.

In the invention, "from once every 3 days to once every 15 days" means once every 3 days, once every 4 days, once every 5 days, once every 6 days, once every 7 days, once every 8 days, once every 9 days, once every 10 days, once every 11 days, once every 12 days, once every 13 days, once every 14 days, or once every 15 days.

It is advantageous to treat the herds suffering from the above-mentioned diseases in a permanent manner. The treatment may, however, be modulated downwards according to the seasons and the activity of the animals (particularly if the animal grazes).

The invention also relates to a composition as defined above, in association with at least one disinfectant, for use in the context of treating diseases involving a parasitic or bacterial podal infection of the ungulates, said at least one disinfectant being used at least 48 hours before said composition is used.

In the invention, prior to the use of the above-mentioned compositions, it is possible to treat the feet of the ungulates with disinfectants. It is thus imperative that the disinfectant is stopped at least 48 hours before the composition according to the invention is used, so as not to kill the bacteria it contains.

The disinfectants used may be those that are commonly used by a person skilled in the art, i.e. antibiotics (for example oxytetracycline for cows), formol, zinc sulfate or copper sulfate, or lime. Other disinfectants known to a person skilled in the art may be used.

The invention will be better understood in the light of the following four examples and 11 figures:

BRIEF DESCRIPTION OF THE DRAWINGS

FIG. 3A shows the proportions at the start of the trial.

FIG. 3B shows the proportions at the end of the trial.

FIG. 6A shows the proportions at the start of the trial.

FIG. 6B shows the proportions at the end of the trial.

FIG. 1A shows the results for the front left foot: column 1: January—healthy 80.1%, problem: 19.9%; column 2: February—healthy 81.4%, problem: 18.6%; column 3: March—healthy 93.1%, problem: 6.9%; column 1: April—healthy 92.9%, problem: 7.1%.

FIG. 1B shows the results for the front right foot: column 1: January—healthy 80.1%, problem: 19.9%; column 2: February—healthy 81.4%, problem: 18.6%; column 3: March—healthy 90.3%, problem: 9.7%; column 1: April—healthy 91.5%, problem: 8.5%.

FIG. 1C shows the results for the rear left foot: column 1: January'healthy 82.6%, problem: 17.4%; column 2: February—healthy 81.1%, problem: 18.9%; column 3: March—healthy 91%, problem: 9%; column 1: April—healthy 88.5%, problem: 11.5%.

FIG. 1D shows the results for the rear right foot: column 1: January—healthy 82.9%, problem: 17.1%; column 2: February—healthy 81.1%, problem: 18.9%; column 3: March—healthy 91.3%, problem: 8.7%; column 1: April—healthy 87.8%, problem: 12.2%.

EXAMPLES

Figure 1:
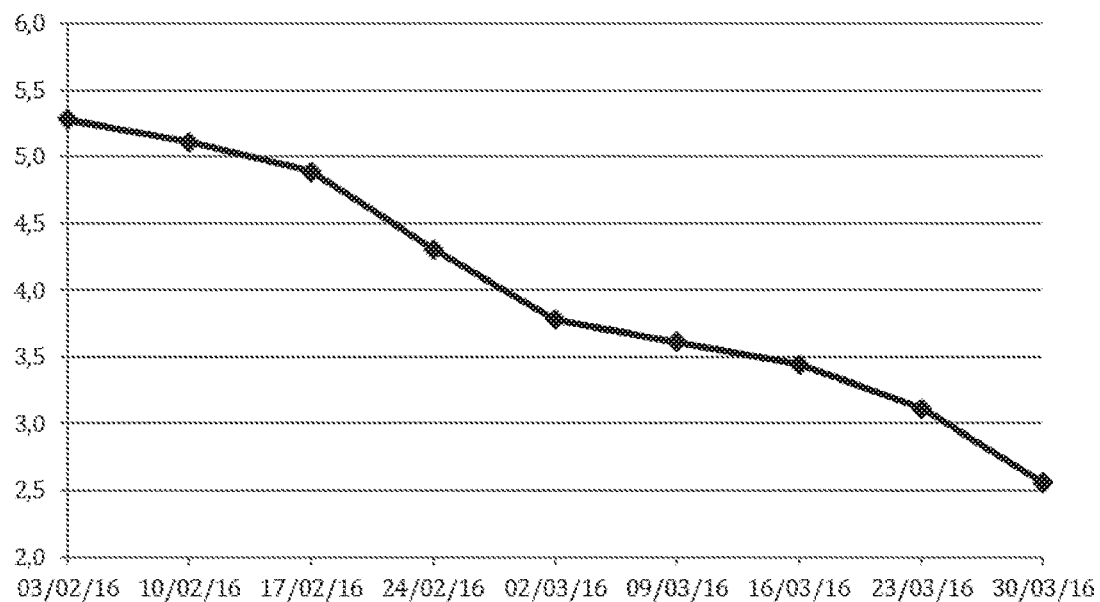
FIG. 1 is a graph showing the progression of the average rating of the condition of the feet of the reference cows on the different dates of treatment with the composition according to the invention.

Example 1: Preparation of the Bacterial Mixtures

In the context of the invention, the inventors prepared flasks in advance containing the following preparations:

Preparation 1=20 ml flask

Mixture of 4 *Bacillus* NOL01, NOL02, NOL03 and NOL04, in sporulated form, at a concentration of from $10^5$ to $10^{11}$ colonies/ml, for each bacterial strain. The four strains are mixed together in equal parts, in the respective proportions 25:25:25:25.

The mixture was kept at a temperature of between −21° C. and −80° C.

Preparation 2=20 ml flask

Lactic bacteria NOL11 ata concentration of from $10^5$ to $10^{11}$ colonies/ml. The bacteria were kept at a temperature of between −21° C. and −80° C.

The inventors then prepared the composition used for the remainder of the experiments:

Mixture: 1 flask of preparation 1+1 flask of preparation 2.

Example 2: Study of the Impact of the Application of the Composition According to the Invention on a Dairy Cattle Herd Suffering from Mortellaro Disease This trial followed the pre-test which showed a reduction in cases of Mortellaro disease in one herd following application of the composition of the invention to the rear feet of the cows. The objective of this new trial is:

to confirm the results on 4 new herds in order to determine the effect of the composition of the invention on Mortellaro disease, to compare the effect of the composition with the preventative treatments that are already used on the herds, to quantitatively measure the efficacy of this treatment.

The trial was carried out on 5 herds of Holstein cows, in which the product was sprayed onto the rear feet of the animals. The effect of the composition of the invention was measured by monitoring the health of the herd (counting and progression of the cases of Mortellaro disease, veterinary treatments), I—Characteristics of the Herds

| Herd 1: Normandy (Calvados; France) interest | |
|---|---|
| Number of cows | 160/170 |
| Milking | 3 Delaval robots |
| Number of batches | 2 |
| Stabling | Straw-bedded stalls |
| Frequency of changing straw bedding | Daily |
| Quantity of straw | High |
| Headlock | Yes, but not for all |
| Scraping | Automatic 3 to 4 times a day |
| Water source | Wellbore |
| Water treatment | No |
| Current Mortellaro treatment | Antibiotic foot bath + robot disinfecting spray |

| Herd 2: Normandy (Calvados; France) | |
| --- | --- |
| Number of cows | 190 |
| Milking | External rotary |
| Number of batches | 2 |
| Stabling | Straw-bedded stalls |
| Frequency of changing straw bedding | — |
| Quantity of straw | Low (straw silage) |
| Headlock | No |
| Scraping | Tractor twice a day |
| Water source | Distribution network |
| Water treatment | — |
| Current Mortellaro treatment | Antibiotic foot bath after washing the feet during milking |

| Herd 3: Normandy (Seine Maritime; France) | |
| --- | --- |
| Number of cows | 190 + dry cows |
| Milking | 3 Delaval robots |
| Number of batches | 2 (130 cows per 2 robots and 60 cows per 1 robot) |
| Stabling | 1st batch in straw-bedded stalls<br>2nd batch in a straw-bedded area |
| Quantity of straw | Moderately low |
| Headlock | Yes |
| Scraping | Automatic |
| Water source | — |
| Water treatment | — |
| Current Mortellaro treatment | Formol foot bath |

| Herd 4: Normandy (Calvados; France) interest | |
| --- | --- |
| Number of cows | 100 |
| Milking | 2 robots |
| Number of batches | — |
| Stabling | Straw-bedded stalls |
| Quantity of straw | Moderate |
| Headlock | Yes |
| Scraping | Automatic |
| Water source | — |
| Water treatment | Treatment against chlorine |
| Current Mortellaro treatment | Dry foot bath |

| Herd 5: Normandy (Calvados; France) | |
| --- | --- |
| Number of cows | 47 + 7 dry cows |
| Milking | 1 Delaval robot |
| Number of batches | 1 |
| Stabling | Straw-bedded stalls |
| Quantity of straw | — |
| Headlock | Yes |
| Scraping | — |
| Water source | Wellbore |
| Water treatment | Treatment against chlorine |
| Current Mortellaro treatment | Antibiotics in a spray can |

II—Product Used and Material

A composition dose according to the invention was prepared from two separate 20 ml flasks:
- flask 1 containing the *Bacillus* NOL01, NOL02, NOL03 and NOL04,
- flask 2 containing the *Lactococcus* NOL11,
- as described in example 1.

The flasks contain the living bacteria in their culture medium. They are provided to the farm in a frozen state and must be kept in a freezer once received. The product is defrosted and diluted in water before nebulization and then sprayed by nebulization. The water used during nebulization must not contain chlorine, and therefore prior treatment of the water with sodium thiosulfate may be necessary.

The trial lasted for 2 months, with a treatment being carried out once a week.

Foot treatments that were carried out by the farmers with antibiotic compositions or with compositions that are incompatible with the bacteria in the composition according to the invention were stopped at least 3 days before the first application of the composition according to the invention (end of week 00). The first application of the product will be carried out in the first week (start of February).

A situational analysis of the health status of the herd was carried out with the farmer before the start of the trial. This assessment constitutes the starting point, and it is from this reference that the progression is evaluated. Since, in most of the herds in the trial, the health status of the herd was being stabilized by an antibiotic treatment or another treatment, this was stopped from the start of the trial.

The farmer reported their observations on the health status of the herd and qualitative records were kept by the technician during their visits. The product finishes being applied in the 9th week.

III—Treatment

Use: to be applied in liquid form. One dose of product (constituted by flasks B and L) is required for each weekly treatment.

The treatment is based on a dose diluted in 5 l of water for treating the rear feet of the cows. The quantity of sprayed product is approximately 25 ml (or approximately 3 seconds of spraying) per foot or approximately 5 l of product for treating the rear feet of 100 dairy cows.

Procedure for preparing the solution:
- Let the product defrost at ambient temperature, between 15 and 25° C., until it is completely liquefied (approx. 1 hour±15 minutes)
- Prepare 5 l of water in the reservoir of the nebulizer and add 80 mg of sodium thiosulfate or 10 ml if a liquid solution (if the water is treated with hydrogen peroxide, always use mineral water or untreated water).
- Take out the capsule and remove the stopper of the flasks
- Pour the two flasks of product into the treated water and add approximately 10 ml of E 133 dye (food-grade bright blue dye).
- Mix to homogenize the product and then let it rest for 15 minutes
- Spray the rear feet of the cows with approximately 25 ml per foot
- This treatment should be repeated every week of the trial (9 treatments in total).

| | Herd 1 | Herd 2 | Herd 3 | Herd 4 | Herd 5 |
| --- | --- | --- | --- | --- | --- |
| Numbers of doses per application | 2 | 2 | 2 | 1 | 1 |
| Quantity of water | 10 l | 10 l | 10 l | 5 l | 5 l (only 2.5 l is sprayed) |
| Quantity of added thiosulfate | 160 mg (2 doses) | 160 mg (2 doses) | 160 mg (2 doses) | 80 mg (1 dose) | 80 mg (1 dose) |
| Quantity of added dye | 8 ml | No dye | 8 ml | 4 ml | 4 ml |

For herd 5, a solution of a dose diluted in 5 l is prepared, which is normally provided for 100 cows, but only half is used for the application, and the rest is disposed of, IV—Description of the Measures and Analyses 1—Common measures for all of the herds Rating of the condition of each reference cow:

On the first day of the trial, around a dozen cows identified by the farmer as severely affected or particularly vulnerable to Mortellaro disease are tracked most closely. An indicative rating of the condition of each cow is given by the farmer on a scale of 0 to 10, with 0 representing a healthy cow and 10 a seriously affected cow.

2—Overall rating of the condition of the herd:

The farmer also gives an overall rating of the condition of their herd on a scale of 0 to 10, with 0 representing a totally healthy herd and 10 for 100% of animals affected.

3—Photos of the cows' feet, application:

Photos of the rear feet of the cows are taken to give an image of the possible observations on the farm and of clinical signs of cases of Mortellaro disease without lifting up the feet. Photos of the preparation and application are also taken.

4—Rating of lameness of the reference cows:

A lameness rating is given for the reference cows in accordance with the following matrix:

0: Good mobility—walks with a uniform distribution of weight and pace on their four feet, with a flat back. The cow can take long, smooth strides.

1: Flawed mobility—non-uniform (in terms of the distribution of weight or pace) or reduced walking ability; affects one or more feet, difficult to identify.

2: Reduced mobility—non-uniform walk on an easily identifiable foot and/or considerably reduced strides (generally associated with an arched back).

3: Severely reduced mobility—incapable of walking as fast as a human walking at a brisk pace (cannot keep up with the healthy herd) and has signs of the score of 2 above.

5—Specific measure for herd 2

Rating of the cows' reaction during washing:

A rating of the cows' reaction is given while the feet are being washed. The lesions found in an acute stage of Mortellaro disease are very sensitive, and therefore the jet of water used when washing diseased feet often provokes a reaction in the cows, which lift up or move their feet. This reaction is therefore recorded for each of the rear feet using the following rating:

No reaction—Slight reaction—Strong reaction

6—Specific measure for herd 5

Photos of the rear feet of all the cows:

At this farm, all of the herd passes into a trimming cage (hired or procedure by a trimmer) and a photo is taken of each rear foot. Using these photos, each foot is rated in accordance with the following matrix:

M0: healthy. Healthy cow without digital dermatitis lesions

M1: early stage. Well-circumscribed lesion, with a "strawberry skin" appearance, pink or grey, less than 2 cm, Generally painful.

M2: acute stage. Lesions which render the cows lame since they are hypersensitive and painful. Localized skin ulceration at the edge of the hoof horn (1) or around the claws (2). Progression: chronic inflammation and growth of the skin in small raised nodules (3) or in filaments (thick hairs) (4). Often covered with pus with a foul odor.

M3: healing stage. Appears after effective treatment; the lesion becomes covered with a black scab and becomes insensitive. The recovery may be complete (return to stage M0) or partial (stage M4)

M4: disease reservoir. Chronic, non-active, dry, and insensitive lesion. Thick skin with growth of thick hairs M4-1: M1 form active on M4 lesion, often without distinct edges.

7—Records taken by the farmer

If the farmer has already regularly made records on problems relating to lameness, they are collected and used to evaluate the effect of the product (e.g. number of lame cows, individual treatment, cow culling for this reason, etc.).

The farmer's perception of the overall effect of the treatment and any observations or remarks are also recorded.

Likewise, if the farmer has a historic record of the frequencies of Mortellaro disease/lameness or veterinary treatments, these data are used to obtain a point of comparison with the period of the trial.

V—Results

Herd 2

Result for herd 2: rating of foot condition

| | Rating of foot condition on a scale of 0 to 10 (0 = NTR (nothing to report), 10 = severe foot problems) | | | | | | | |
|---|---|---|---|---|---|---|---|---|
| Cow no. | 3 Feb. 2016 | 10 Feb. 2016 | 17 Feb. 2016 | 24 Feb. 2016 | 2 Mar. 2016 | 9 Mar. 2016 | 16 Mar. 2016 | 23 Mar. 2016 | 30 Mar. 2016 |
| 8480 | 0 | 0 | 0 | 0 | 0 | 0 | 0 | 0 | 0 |
| 6264 | 7 | 7 | 6 | 5 | 5 | 5 | 5 | 4 | 2 |
| 5959 | 4 | 4 | 3 | 3 | 2.5 | 2 | 2 | 1 | 1 |
| 6300 | 9 | 9 | 9 | 8 | 7 | 6 | 6 | 5 | 5 |
| 6271 | 9 | 9 | 9 | 8 | 8 | 8 | 8 | 8 | 8 |
| 6367 | 4 | 4 | 3 | 3 | 3 | 4 | 5 | 5 | 4.5 |
| 6244 | 7 | 7 | 7 | 6 | 6 | 6 | 5 | 5 | 5 |
| 6209 | 4 | 4 | 4 | 3 | 2 | 1 | 1 | 1 | 0 |
| 6242 | 9 | 9 | 9 | 8.5 | 7 | 7 | 7 | 7 | 7 |
| 4834 | 8 | 6 | 5 | 5 | 4 | 5 | 5 | 4 | 2 |
| 8535 | 4 | 4 | 4 | 3 | 2 | 2 | 2 | 1.5 | 1 |
| 6010 | 4 | 5 | 5 | 5 | 4 | 4 | 3 | 2 | 2 |
| 0750 | 4 | 4 | 3 | 3 | 2 | 2 | 1 | 1 | 1 |
| 6289 | 6 | 5 | 5 | 4 | 4.5 | 4 | 4 | 4.5 | 4 |
| 4837 | 4 | 4 | 4 | 3 | 2 | 2 | 2 | 1 | 1 |
| 6232 | 4 | 3 | 3 | 2 | 2 | 2 | 2 | 2 | 0 |
| 5993 | 4 | 4 | 3 | 2 | 2 | 1 | 1 | 1 | 0 |
| 6416 | 4 | 4 | 6 | 6 | 5 | 4 | 3 | 3 | 2.5 |

An average increase of 2.7 points is observed for the problem cows, with the lameness of 16 cows out of 18 having reduced. The two others were in a stable condition.

The progression of the average rating over the course of the trial is shown in FIG. 1.

Results on lameness: rating of lameness

| | Rating of lameness between 0 and 3 (cf. matrix) | | |
|---|---|---|---|
| Cow no. | 3 Feb. 2016 | 24 Feb. 2016 | 30 Mar. 2016 |
| 8480 | 0 | 0 | 0 |
| 6264 | 2 | 1 | 1 |
| 5959 | 1 | 0 | 0 |
| 6300 | 2.5 | 3 | 2.5 |
| 6271 | 3 | 2 | 2 |
| 6367 | 1 | 1 | 1 |
| 6244 | 2 | 1 | 2 |
| 6209 | 1 | 0 | 0 |
| 6242 | 3 | 3 | 2 |

-continued

| | Rating of lameness between 0 and 3 (cf. matrix) | | |
|---|---|---|---|
| Cow no. | 3 Feb. 2016 | 24 Feb. 2016 | 30 Mar. 2016 |
| 4834 | 3 | 2 | 0 |
| 8535 | 1 | 1 | 1 |
| 6010 | 1 | 2 | 1 |
| 0750 | 1 | 1 | 0 |
| 6289 | 2 | 2 | 2 |
| 4837 | 1 | 2 | 0 |
| 6232 | 1 | 0 | 0 |
| 5993 | 1 | 1 | 0 |
| 6416 | 1 | 2 | 1 |

Figure 2:
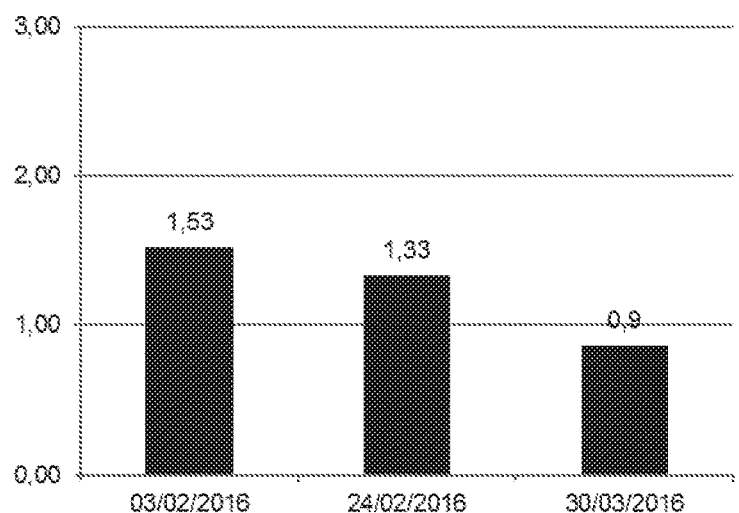
FIG. 2 is a bar graph showing the progression of the average rating of the lameness of the reference cows on the different dates of treatment with the composition according to the invention.
Figures 3A, 3B:
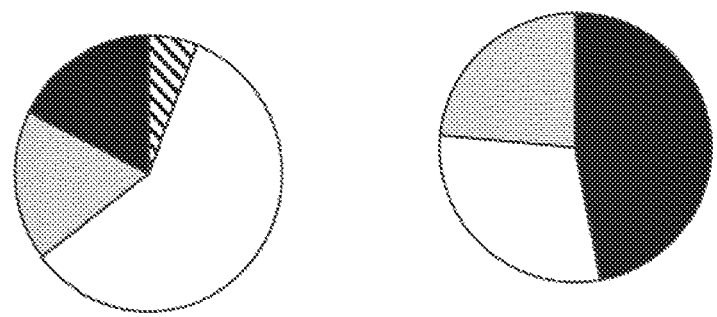
FIGS. 3A and 3B are pie charts showing the distribution of the 4 categories of lameness for the reference cows. The different categories are as follows: category 0 is in black, category 1 is in white, category 2 is in gray and category 3 is shaded.

At the end of the trial, the lameness category of 11 cows out of 18 had reduced, and no aggravation was observed in the monitored cows. The results are shown in FIGS. 2 and 3A to 3B.

The results for this herd are very positive.

Before treatment with the composition according to the invention, the cows received the following treatment once a week:

1. Washing of the cows' feet in the milking parlor
2. Formol foot baths, copper sulfate and zinc sulfate with the foot bath being changed between the 2 batches During the trial, the animals were treated in the following manner once per week:

1—Washing of the cows' feet in the milking parlor (only the 1st half of the trial)
2—Application of the composition according to the invention in the milking parlor with the sprayer.

The treatment according to the invention has made it possible to go from 7 to 8 oxytetracycline treatments a week to one treatment once or three times during the same period. Although the odor of infection of the cows was very present before the trial, this odor was largely reduced, According to the farmer, without the washing of the cows' feet in the milking parlor, the application of the microflora with the material used is less restrictive than the foot-bath system Regarding trimming, all of the herd underwent trimming 2 weeks before the end of the trial without the trimmers being informed of the trial. The trimmers concluded that this was the first year in which they did not mention problems relating to dermatitis (contamination <5% of the herd).

Herd 3

Result for herd 3: rating of foot condition

| | Rating of foot condition on a scale of 0 to 10 (0 = NTR (nothing to report), 10 = severe problems with the feet) | | | | | | | |
|---|---|---|---|---|---|---|---|---|
| Cow no. | 3 Feb. 2016 | 10 Feb. 2016 | 17 Feb. 2016 | 24 Feb. 2016 | 2 Mar. 2016 | 9 Mar. 2016 | 16 Mar. 2016 | 23 Mar. 2016 | 30 Mar. 2016 |
| 1758 | 10 | 8 | 5 | 5 | 5 | 5 | 5 | 10 | 10 |
| 0751 | 5 | 3 | 2 | 1 | 1 | 0 | 0 | 0 | 0 |
| 9086 | 6 | 3 | 2 | 2 | 2 | 0 | 0 | 0 | 0 |
| 9152 | 6 | 3 | 3 | 3 | 2 | 0 | 0 | 0 | 0 |
| 5376 | 2 | 2 | 2 | 2 | 2 | 3 | 2 | 1 | 0 |
| 0227 | 5 | 5 | 5 | 5 | 4 | 3 | 2 | 2 | 0 |
| 0226 | 5 | 8 | 8 | 8 | 7 | 7 | 7 | 8 | 8 |
| 9144 | 8 | 5 | 8 | 8 | 8 | 7 | 7 | 7 | 8 |
| 3589 | 8 | 8 | 8 | 8 | 10 | 10 | 9 | 7 | 2 |
| 0216 | 8 | 8 | 8 | 8 | 8 | 8 | 8 | 8 | 8 |
| 0366 | 6 | 5 | 5 | 5 | 4 | 4 | 3 | 0 | 0 |
| 9460 | 8 | 7 | 7 | 7 | 7 | 6 | 6 | 5 | 6 |
| 0294 | 2 | 2 | 2 | 2 | 1 | 1 | 1 | 1 | 0 |
| 1787 | | 9 | 9 | 9 | 6 | 5 | 5.5 | 8 | 8 |

An average increase of 2.9 points is observed for the problem cows. 11 cows out of 14 have an improved foot condition, except in the last 2 weeks. In the last two weeks, problems with scraping led to deterioration in the cleanliness of the living areas, which probably increased the environmental bacterial count and had an impact on the condition of 2 reference cows.

Figure 4:
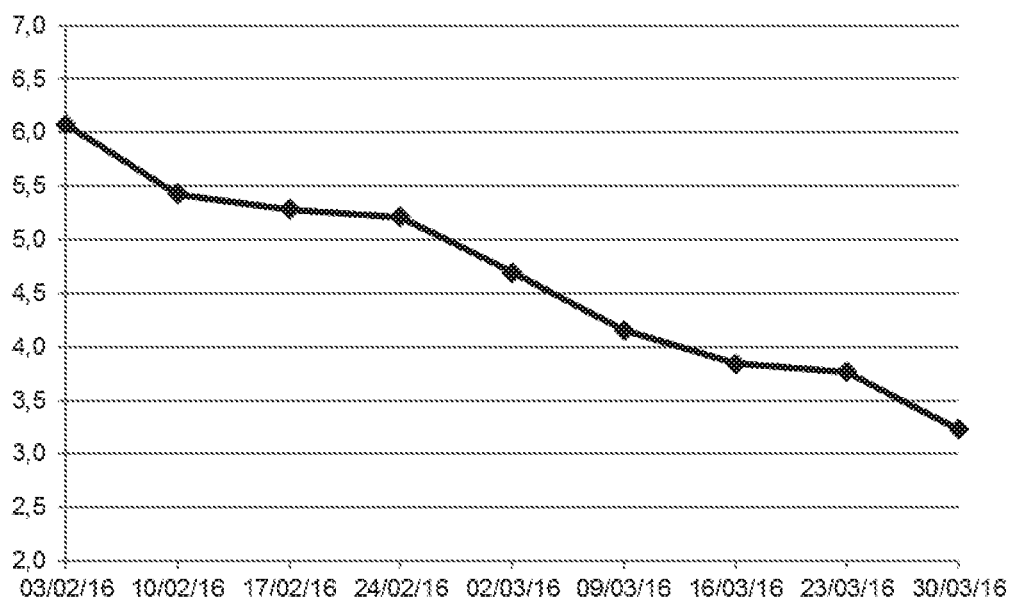
FIG. 4 is a graph showing the progression of the average rating of the condition of the feet of the reference cows on the different dates of treatment with the composition according to the invention.

The progression of the average rating over the course of the trial is shown in FIG. 4.

Results on lameness: rating of lameness

| | Rating of lameness between 0 and 3 (cf. matrix) | | |
|---|---|---|---|
| Cow no. | 3 Feb. 2016 | 24 Feb. 2016 | 30 Mar. 2016 |
| 1758 | 3 | 2 | 3 |
| 0751 | 3 | 1 | 0 |
| 9086 | 1 | 1 | 0 |
| 9152 | 2 | 1 | 0 |
| 5376 | 2 | 2 | 1 |
| 0227 | 0 | 0 | 0 |
| 0226 | 2 | 3 | 3 |
| 9144 | 2 | 2 | 3 |
| 3589 | 1 | 2 | 0 |
| 0216 | 3 | 3 | 3 |
| 0366 | 3 | 2 | 0 |
| 9460 | 2.5 | 2 | 1 |

-continued

| | Rating of lameness between 0 and 3 (cf. matrix) | | |
|---|---|---|---|
| Cow no. | 3 Feb. 2016 | 24 Feb. 2016 | 30 Mar. 2016 |
| 0294 | 2 | 2 | 0 |
| 1787 | | 3 | 3 |

Figure 5:
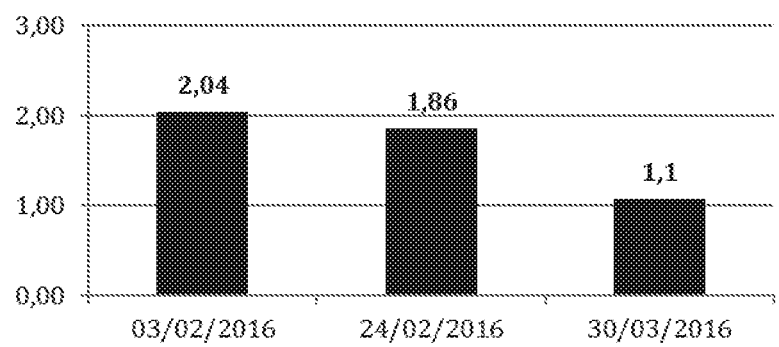
FIG. 5 is a bar graph showing the progression of the average rating of the lameness of the reference cows on the different dates of treatment with the composition according to the invention.
Figures 6A, 6B:
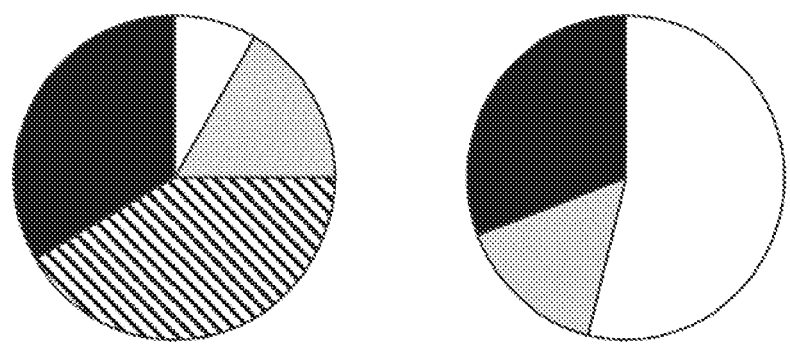
FIGS. 6A and 6B are pie charts showing the distribution of the 4 categories of lameness for the reference cows. The different categories are as follows: category 0 is in white, category 1 is shaded, category 2 is in black and category 3 is in black.

At the end of the trial, 9 cows out of 14 had better mobility, 3 had not changed, and 2 had deteriorated. It should however be noted that there was an improvement by one category for all the reference cows. The results are shown in FIGS. 5 and 6A to 6B.

The results for this herd are also very positive.

Before treatment with the composition according to the invention, the cows received formol foot baths as a treatment.

During the trial, the animals were treated in the following manner once per week in the headlock by applying the composition according to the invention using the sprayer.

According to the farmer, before treatment, numerous cases of lameness occurred regularly. After treatment, only 2 to 3 cows had problems, and only a few cows did not respond well to the composition.

The farmer is convinced of the efficacy of the composition, even though he was skeptical before the trial.

Herd 5
Result for herd 5: rating of foot condition

| | Rating of foot condition on a scale of 0 to 10 (0 = NTR (nothing to report), 10 = severe problems with the feet) | | | | | | |
|---|---|---|---|---|---|---|---|
| Cow no. | 10 Feb. 2016 | 17 Feb. 2016 | 24 Feb. 2016 | 2 Mar. 2016 | 9 Mar. 2016 | 16 Mar. 2016 | 23 Mar. 2016 |
| 5722 | 10 | 9 | 9 | 9 | 9 | 9 | 9 |
| 2095 | 8 | 7 | 6 | 5 | 4 | 4 | 3 |
| 5377 | 8 | 8 | 7 | 5 | 4 | 3 | 3 |
| 5794 | 8 | 8 | 7 | 5 | 5 | 5 | 5 |
| 2105 | 7 | 6 | 6 | 4 | 3 | 3 | 2 |
| 5795 | 8 | 6 | 6 | 5 | 4 | 3 | 2 |
| 5801 | 10 | 7.5 | 7 | 6 | 6 | 6 | 5 |
| 5728 | 7 | 6 | 6 | 6 | 6 | 5 | 3 |
| 5788 | 7 | 6 | 5 | 4 | 4 | 3 | 3 |
| 1937 | 6.5 | 6 | 5 | 3.5 | 3 | 2 | 1 |
| 2082 | 7 | 7 | 6 | 4.5 | 3 | 3 | 2 |
| 1826 | 8 | 7 | 6 | 6 | 6 | 5 | 5 |
| 2077 | 7 | 6 | 6 | 4.5 | 3 | 2.5 | 2 |
| 5581 | 4 | 4 | 3.5 | 2 | 1.5 | 1 | 1 |
| 2029 | 4 | 3 | 2 | 1.5 | 1 | 1 | 1 |
| 2108 | | | 10 | 8 | 6 | 4 | 3 |

An average increase of 4.2 points is observed for the problem cows, with 15 cows out of 16 showing an improvement in the condition of their feet. Only one cow remained in a poor condition.

Figure 7:
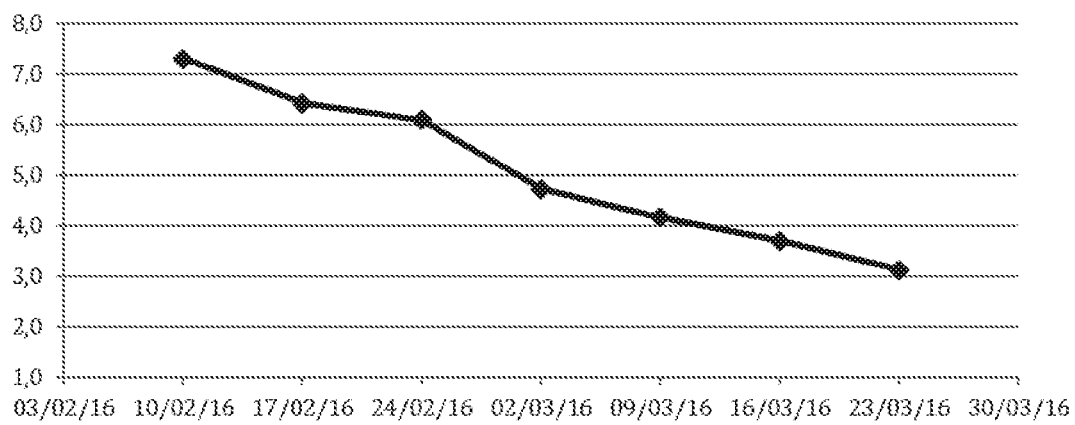
FIG. 7 is a graph showing the progression of the average rating of the condition of the feet of the reference cows on the different dates of treatment with the composition according to the invention.

The progression of the average rating over the course of the trial is shown in FIG. 7.

The results for this herd are again very positive here.

Before treatment with the composition according to the invention, the cows received an application of disinfectant by robot (4 Hooves).

During the trial, the animals were treated in the following manner once per week in the headlock by applying the composition according to the invention using the sprayer.

Before the treatment, the cows that were severely affected were treated individually with oxytetracycline. None of these treatments were necessary after application of the composition according to the invention.

According to the farmer, there was good improvement in the heard, and in fact considerably fewer cows have to be accompanied as far as the milking parlor.

Herd 1: the farmer wanted to stop the trial, since he had to stop his former practices (daily disinfection, alternating every week between peroxide and bleach) and he saw deterioration in the condition of his herd after a single week.

Herd 3: the trial was stopped since the inventors saw that the farmer had changed absorbent in his stalls, switching from a conventional absorbent to slaked lime applied in the morning and evening. Since slaked lime has disinfectant properties, it was therefore incompatible with the composition of the invention. The farmer chose to stop the trial rather than to stop the lime.

Figure 8:
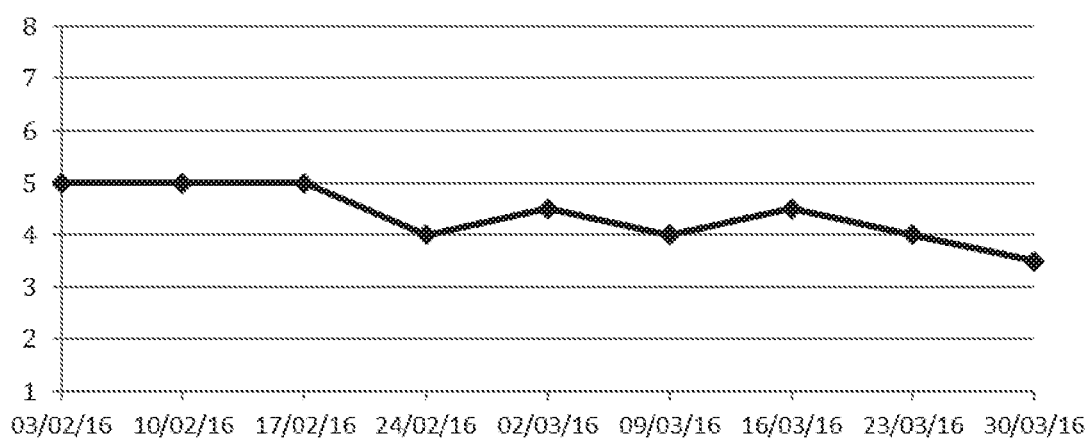
FIG. 8 is a graph showing the progression of the average rating of the condition of the feet of the cows in the herd on the different dates of treatment with the composition according to the invention.
Figure 9:
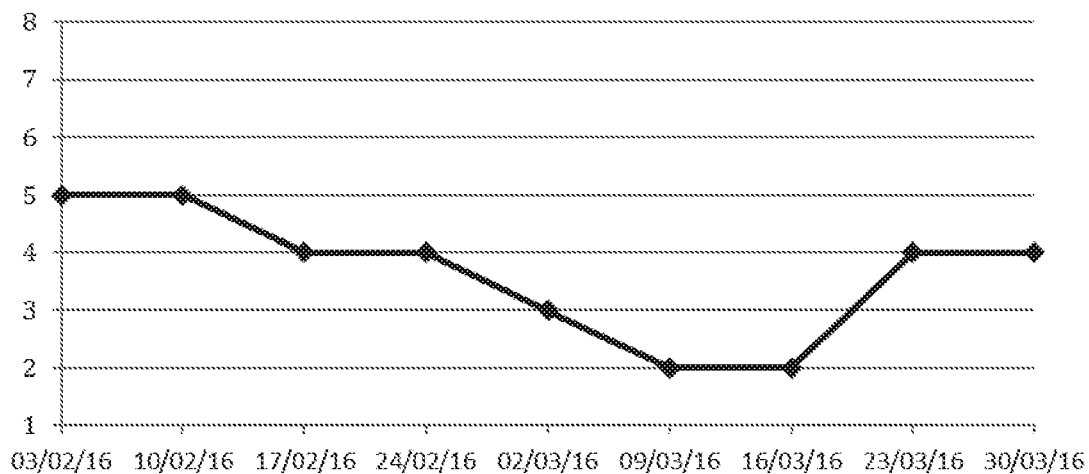
FIG. 9 is a graph showing the progression of the average rating of the condition of the feet of the cows in the herd on the different dates of treatment with the composition according to the invention.
Figure 10:
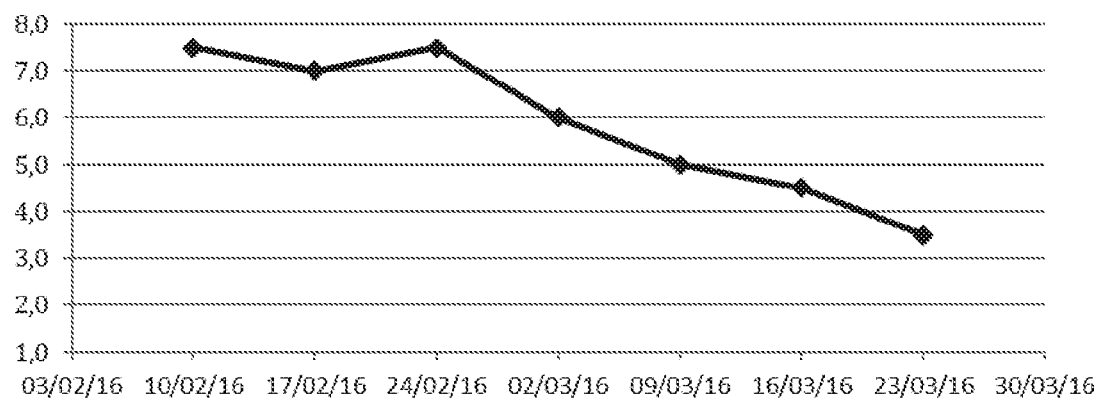
FIG. 10 is a graph showing the progression of the average rating of the condition of the feet of the cows in the herd on the different dates of treatment with the composition according to the invention.

FIGS. 8 to 10 show the overall progression of the herds on the 3 farms.

These results, following an application of the composition according to the invention, are only visible approximately 3 weeks after the first application, which is the time required for the bacteria contained in the composition according to the invention to implant.

Stopping a former regular treatment that stabilized the condition of the herd risks resulting in deterioration in the 2 first weeks of treatment with the composition according to the invention. It may therefore be necessary to individually treat each cow.

Example 3: Test of Reducing the Frequency of Application

The inventors wanted to test if reducing the frequency of application to once every 2 weeks allows a stabilized situation to be maintained after 2 months of weekly application.

To do this, the protocol described in the previous example was slightly modified. For herd 2, from Mar. 30, 2016, the farmer switched to one application every 2 weeks with an equivalent dosage (2 doses for 100 cows used for the 190 cows in the herd).

For herd 5, from Apr. 15, 2016, the farmer switched to one application every 2 weeks with an equivalent dosage (1 dose for 100 cows for the 55 cows in the herd).

Herd 3:

The condition of the reference cows continued to improve and stabilized with a good foot condition following the reduction of the treatment. Furthermore, the general condition of the herd stabilized with a good foot condition.

From April, the cows went outside.

The switch from one application every week to one application every two weeks stabilized the overall situation of the herd with a good condition in relation to foot problems. No deterioration was observed.

Figure 11:
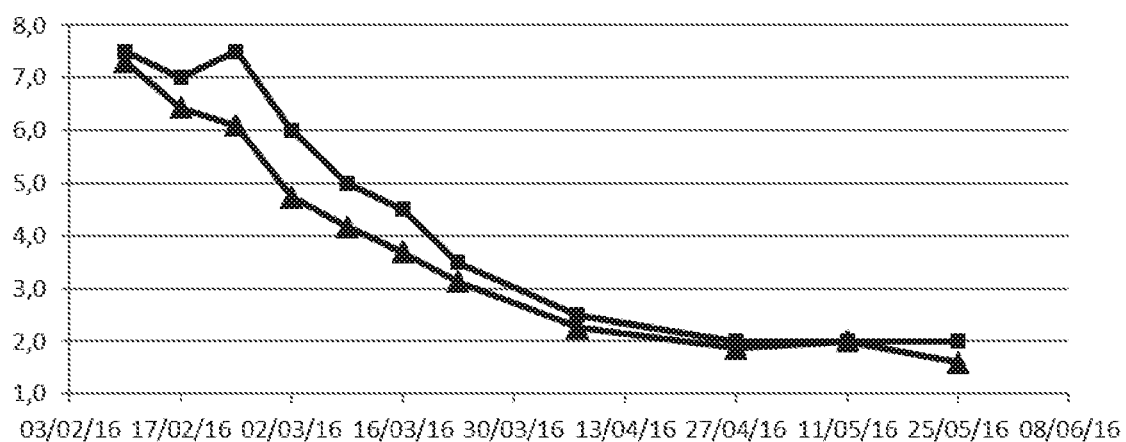
FIG. 11 is a graph showing the progression of the average rating of the condition of the feet of the reference cows (curve with triangles) and the cows in the herd (curve with squares) on the different dates of treatment with the composition according to the invention.
Figure 12:
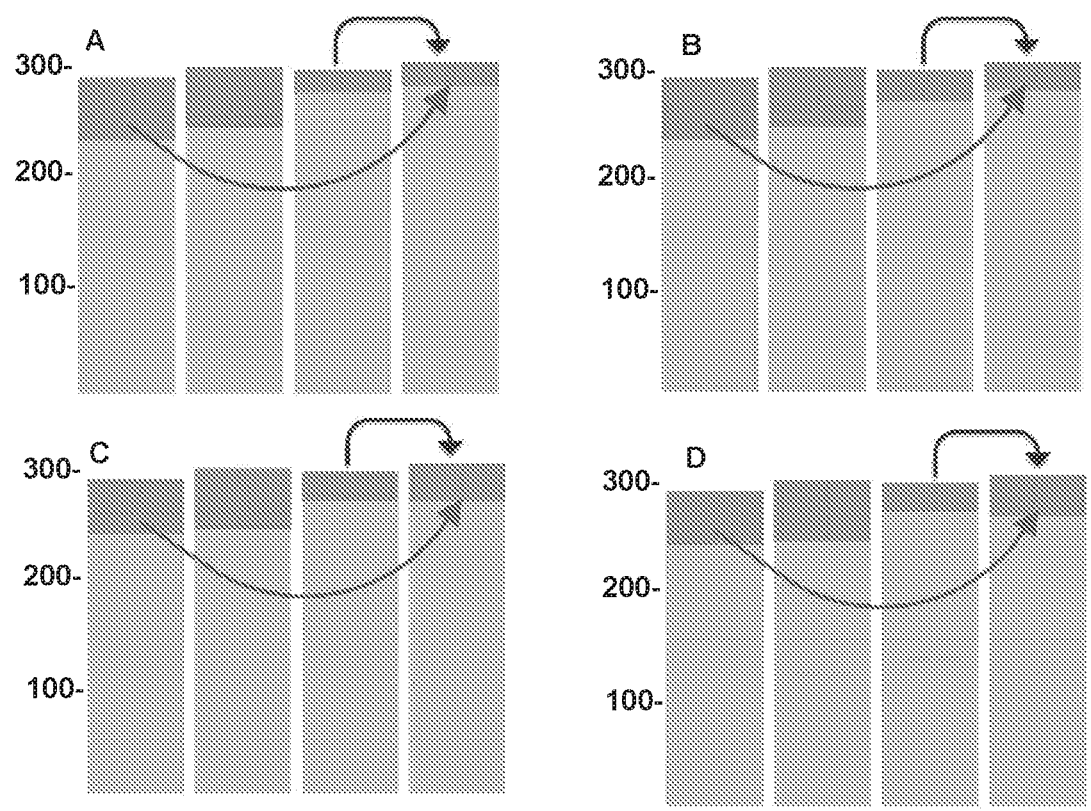
FIG. 12A to 12D show graphs showing the proportions of healthy feet (light gray) and of problem feet (dark gray) for each of the four feet of the sheep, for each month after the start of the treatment.

The results are shown in FIG. 11.

The following table shows the values obtained:

| Cow no. | 10 Feb. 2016 | 17 Feb. 2016 | 24 Feb. 2016 | 2 Mar. 2016 | 9 Mar. 2016 | 16 Mar. 2016 | 23 Mar. 2016 | 7 Apr. 2016 | 27 Apr. 2016 | 11 May 2016 | 25 May 2016 |
|---|---|---|---|---|---|---|---|---|---|---|---|
| 5722 | 10 | 9 | 9 | 9 | 9 | 9 | 9 | 9 | 7 | 7 | 6 |
| 2095 | 8 | 7 | 6 | 5 | 4 | 4 | 3 | 2 | 2 | 2 | 2 |

-continued

| Cow no. | 10 Feb. 2016 | 17 Feb. 2016 | 24 Feb. 2016 | 2 Mar. 2016 | 9 Mar. 2016 | 16 Mar. 2016 | 23 Mar. 2016 | 7 Apr. 2016 | 27 Apr. 2016 | 11 May 2016 | 25 May 2016 |
|---|---|---|---|---|---|---|---|---|---|---|---|
| 5377 | 8 | 8 | 7 | 5 | 4 | 3 | 3 | 3 | 3 | 3 | 2 |
| 5794 | 8 | 8 | 7 | 5 | 5 | 5 | 5 | 4 | 2 | 2 | 2 |
| 2105 | 7 | 6 | 6 | 4 | 3 | 3 | 2 | 1 | 1 | 2 | 1 |
| 5795 | 8 | 6 | 6 | 5 | 4 | 3 | 2 | 1 | 1 | 1 | 1 |
| 5801 | 10 | 7.5 | 7 | 6 | 6 | 6 | 5 | 4 | 3 | 3 | 2 |
| 5728 | 7 | 6 | 6 | 6 | 6 | 5 | 3 | 2 | 2 | 3 | 2 |
| 5788 | 7 | 6 | 5 | 4 | 4 | 3 | 3 | 2 | 2 | 2 | 2 |
| 1937 | 6.5 | 6 | 5 | 3.5 | 3 | 2 | 1 | 0 | 0 | 0 | 0 |
| 2082 | 7 | 7 | 6 | 4.5 | 3 | 3 | 2 | 1 | 1 | 1 | 1 |
| 1826 | 8 | 7 | 6 | 6 | 6 | 5 | 5 | 4 | 3 | 3 | 2 |
| 2077 | 7 | 6 | 6 | 4.5 | 3 | 2.5 | 2 | 1 | 1 | 1 | 1 |
| 5581 | 4 | 4 | 3.5 | 2 | 1.5 | 1 | 1 | 0 | 0 | 0 | 0 |
| 2029 | 4 | 3 | 2 | 1.5 | 1 | 1 | 1 | 0 | 0 | 0 | 0 |
| 2108 |  |  | 10 | 8 | 6 | 4 | 3 | 3 | 2 | 2 | 2 |

For herd 1:

After a transition phase, which required antibiotic treatments followed by a protocol for intensified application of the composition of the invention (feet+building), the general condition of the herd improved considerably.

According to the farmer, he was seeing a situation that he had not experienced for a year and a half. He tried spacing out the applications slightly by switching to 10/12 days, but he observed that it was not possible to go beyond 12 days since the feet started to turn pink, which is a sign of the symptoms reappearing.

For herd 5:

Severe deterioration was observed in the health status of the herd due to poor upkeep of the stabling, resulting from human error.

Control was regained of the farm and intensified application of the applications to the feet and the environment was carried out for 1 month with the composition according to the invention in order to restore the health status of the herd.

The current condition of the herd has improved, and trimming of the herd has begun.

In a period in which the cows had access to pasture, the pathogenic count was lower (frequenting soiled areas less), and application every 2 weeks or more did not cause any deterioration in the foot condition of the herd.

Example 4: Study of the Impact of the Application of the Composition According to the Invention to an Ovine Herd In this example, the inventors wanted to test the efficiency of the composition according to the invention for treating or improving lameness in sheep, within the context of foot rot.

The trial was carried out on a herd of 300 of the Lacaune breed of sheep, on a farm in the Pyrenees-Atlantiques department.

The sheep were treated with the composition according to the invention by an application of the microflora once a week for 12 weeks by means of a foot-bath mat. On each application day, the sheep passed over the mat twice (once per milking).

The bacteria constituting the composition according to the invention are used at a rate of one dose representing 40 ml of the composition as described in example 1, in 30 l of water with a bright blue E133 dye and thiosulfate, and then the solution was poured into the foot bath.

Results

The overall results are set out in the following table:

|  | January | February | March | April |
|---|---|---|---|---|
| Number of sheep | 281 | 291 | 288 | 295 |
| Problem sheep | 91 | 106 | 94 | 113 |
| No problems | 190 | 185 | 194 | 182 |
| 1 foot | 5 | 0 | 89 | 110 |
| 2 feet | 69 | 103 | 5 | 3 |
| 3 feet | 3 | 0 | 0 | 0 |
| 4 feet | 14 | 3 | 0 | 0 |

It was found that the proportions are as follows:

|  | January | February | March | April |
|---|---|---|---|---|
| No problems | 68% | 64% | 67% | 62% |
| 1 foot | 2% | 0% | 31% | 37% |
| 2 feet | 25% | 35% | 2% | 1% |
| 3 feet | 1% | 1% | 0% | 0% |
| 4 feet | 5% | 0% | 0% | 0% |

2×2 chi-squared test between the dates on the distribution of the sheep by number of problem feet:

| p-value | January | February | March | April |
|---|---|---|---|---|
| January | / |  |  |  |
| February | 2.26E−04 | / |  |  |
| March | 2.20E−16 | 2.20E−16 | / |  |
| April | 2.20E−16 | 2.20E−16 | 0.2214 | / |

The distributions are significantly different between the dates, except for between March and April.

The sheep with problems on the first day of the trial almost all improved in terms of the number of problem feet.

However, deterioration is possible in the first weeks following a previous treatment being stopped.

Between the start and end of the trial, of the 82 problem sheep present for the entirety of the trial, 79 experienced a reduction in category. The problem sheep at the end of the trial were different sheep.

The results, broken down foot by foot, are set out in FIG. 12A to 12D.

These results show that 96% of the problem sheep at the start of the trial present for the entirety of the trial had at least one problem foot fewer after the treatment.

In addition, at the end of the trial, there were no sheep with 2 or more problem feet.

Together, these results show the efficacy of the composition according to the invention on the problem of lameness.

The invention is not limited to the embodiments set out here, and other embodiments will be clear to a person skilled in the art.

The invention claimed is:

1. A method for preventing diseases involving a parasitic or bacterial podal infection in the feet of ungulates or for improving condition of said ungulates suffering from diseases involving a parasitic or bacterial podal infection in the feet, said method comprising the application to a foot of an ungulate a therapeutically effective amount of a bacterial composition comprising a bacterial mixture, wherein the bacterial composition comprises:
- a lactic bacterium *Lactococcus lactis* spp *lactis* 1 strain NOL11 as filed at the CNCM (Institut Pasteur, Paris) according to Budapest Treaty on 14 Mar. 2012 under the number CNCM I-4609;
and
- the *Bacillus subtilis* strains NOL01, NOL02, NOL03 and NOL04 as filed at the CNCM according to Budapest Treaty on 14 Mar. 2012 under the respective numbers CNCM I-4606, CNCM I-5043, CNCM I-4607, and CNCM I-4608, wherein said application is repeated at intervals of 3 to 15 days.

2. The method according to claim 1, said composition containing from $10^5$ to $10^{11}$ bacterial *Bacillus* colonies and from $10^5$ to $10^{11}$ lactic-bacteria colonies, the bacterial colonies being by ml or g of composition.

3. The method according to claim 1, wherein said at least one *Bacillus* strain is in sporulated form and/or in vegetative form.

4. The method according to claim 1, wherein said diseases involving a parasitic or bacterial infection in the feet of ungulates are selected from: Mortellaro disease, interdigital dermatitis, tyloma, paronychia, laminitis, foot rot, bulb erosion, toe necrosis, and pododermatitis.

5. The method according to claim 1, said composition being in a liquid form for application on a foot of the ungulate or used in a basin in which the feet of the ungulates are soaked.

6. The method according to claim 1, wherein said composition is diluted with from 1 to 5 liters of liquid for 50 to 60 animals.

7. The method according to claim 1, comprising a step of application of at least one disinfectant for treating diseases involving a parasitic or bacterial podal infection of an ungulate, wherein said at least one disinfectant is applied at least 48 hours before application of said composition.

* * * * *